United States Patent [19]

Schultz et al.

[11] Patent Number: 4,641,646
[45] Date of Patent: Feb. 10, 1987

[54] ENDOTRACHEAL TUBE/RESPIRATOR TUBING CONNECTING LOCK MECHANISM AND METHOD OF USING SAME

[75] Inventors: Kenneth E. Schultz, Dauphin, Pa.; William R. Evans, Mooresville, N.C.

[73] Assignee: Kenneth E. Schultz, Camp Hill, Pa.

[21] Appl. No.: 720,310

[22] Filed: Apr. 5, 1985

[51] Int. Cl.⁴ .................. A61M 16/00; F16L 35/00
[52] U.S. Cl. .................. 128/207.14; 128/DIG. 26; 128/204.18; 285/114; 604/283; 604/905; 24/17 A; 24/17 AP; 24/30.5 P
[58] Field of Search .............. 128/207.14, 207.15, 128/207.16, 207.17, 204.26, 200.26, 204.18, 200.24, DIG. 26; 285/114, 423; 24/17 A, 17 AP, 30 SP; 604/93, 905, 283

[56] References Cited

U.S. PATENT DOCUMENTS

| | | | |
|---|---|---|---|
| 1,313,610 | 8/1919 | St. Clair et al. | 128/DIG. 26 |
| 1,529,793 | 3/1925 | Jardine et al. | 285/114 |
| 4,093,282 | 6/1978 | Kryiakodis | 285/114 |
| 4,109,941 | 8/1978 | Wood et al. | 285/114 |
| 4,307,903 | 12/1981 | Wallace | 128/207.14 |
| 4,449,527 | 5/1984 | Hinton | 128/207.17 |
| 4,516,293 | 5/1985 | Beran | 128/207.17 |

FOREIGN PATENT DOCUMENTS 92803 2/1962 Denmark ............. 128/200.26

Primary Examiner—Henry J. Recla
Attorney, Agent, or Firm—Wigman & Cohen

[57] ABSTRACT

The present invention relates to a locking mechanism for locking an endotracheal tube to a respirator, and the method of using the same. The locking mechanism comprises two clamp mechanisms and a strap interconnecting them. One of the clamp mechanisms is tightened around the endotracheal tube, and the other clamp mechanism is a quick-release clamp that is clamped onto the respirator connector in a quickly releasable manner.

19 Claims, 7 Drawing Figures

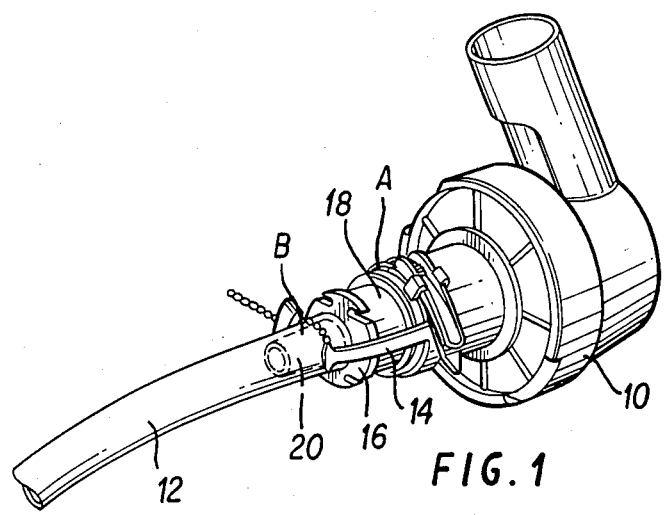
FIG. 1
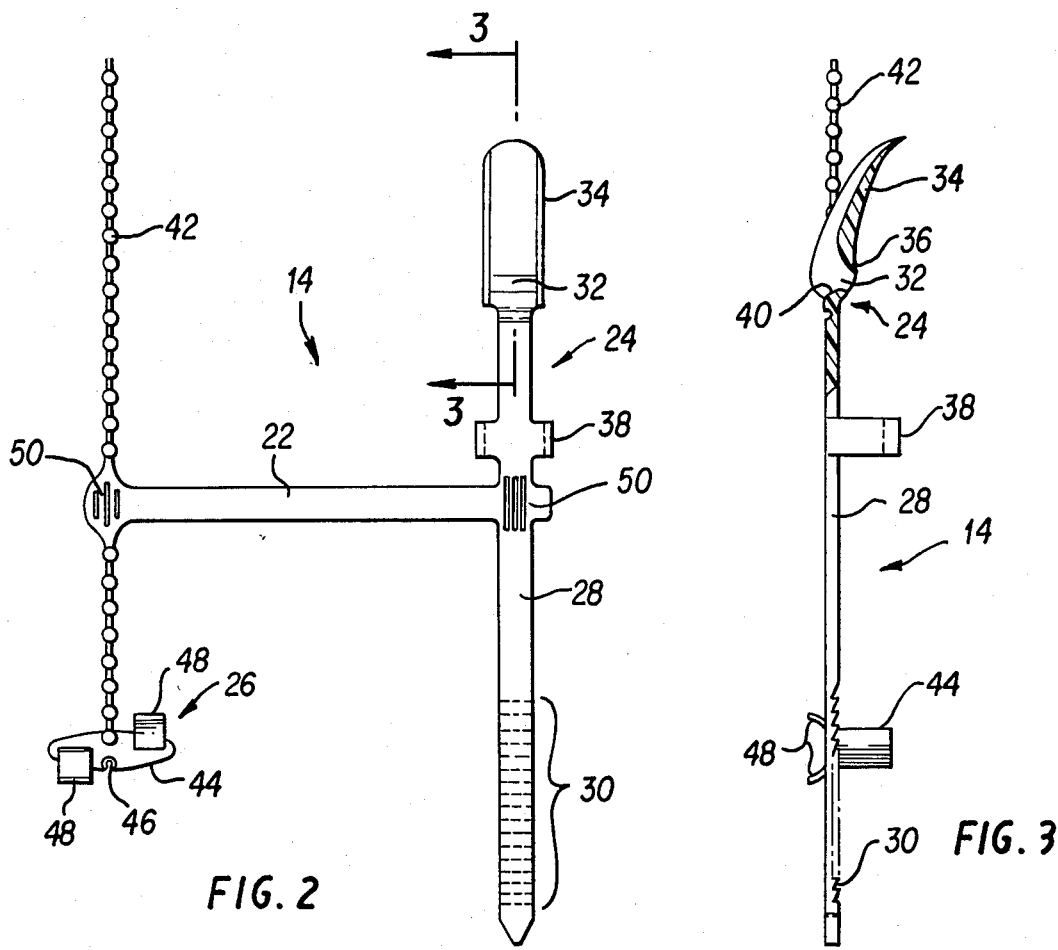
FIG. 2
FIG. 3

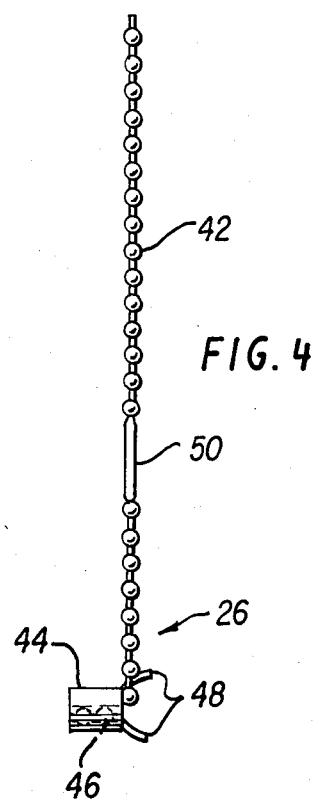
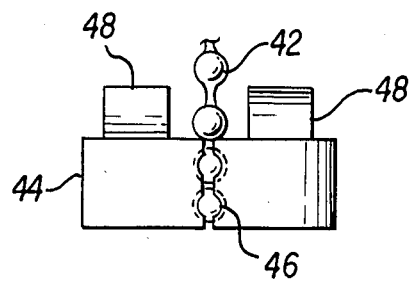
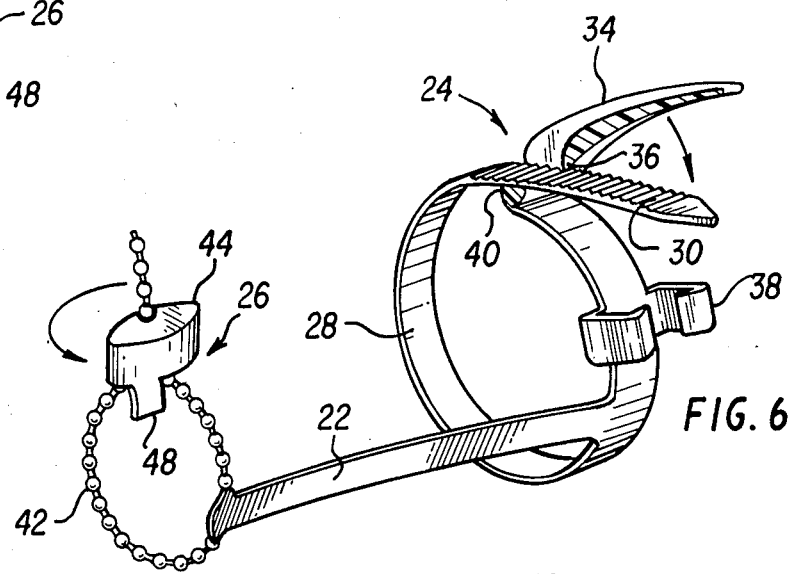
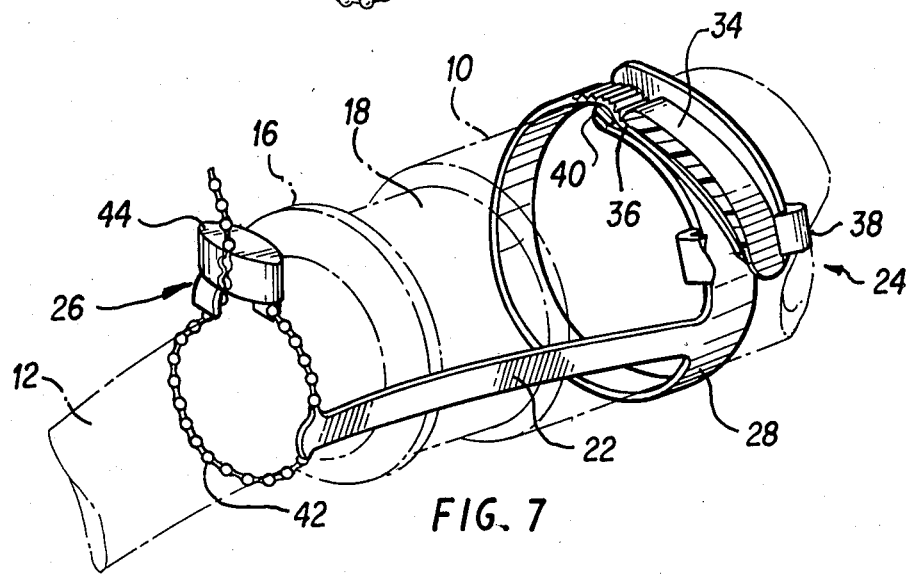
FIG. 4
FIG. 5
FIG. 6
FIG. 7

ENDOTRACHEAL TUBE/RESPIRATOR TUBING CONNECTING LOCK MECHANISM AND METHOD OF USING SAME

BACKGROUND OF THE INVENTION

The present invention relates to a connecting lock mechanism for an endotracheal tube and a respirator tubing connector, and a method of using the same, and in particular, to a connecting lock mechanism for maintaining a physical connection between an endotracheal tube and a respirator tubing.

For certain surgical procedures and in certain critical care conditions, patients require an endotracheal tube that is connected to a respirator or mechanical breathing apparatus. The connection between the endotracheal tube and the respirator tubing must be secure enough so that it does not accidentally become disconnected, since such a disconnection can result in injury or death to the patient. However, the connection must also be able to be quickly uncoupled and recoupled, since in case of secretions forming in the patient's trachea and bronchi, the respirator must be quickly uncoupled from the endotracheal tube so that suction can be applied to the endotracheal tube to withdraw the secretions.

Conventional respirator tube/endotracheal tube connectors usually comprise a semi-rigid plastic coupling having a slightly tapered tube at one end, over which a flexible plastic endotracheal tube is mounted with a friction fit. At the other end of the coupling is a tubular projection which fits into a rigid plastic respirator connector that is connected to a respirator or mechanical breathing system. A frequent problem that occurs with such a connector is the accidental uncoupling of either the endotracheal tube or the respirator conector from the coupling, thereby cutting off the flow of air to the patient.

Connecting lock mechanisms for respirator/endotracheal tube connections are known in the art. Examples of the prior art connecting lock mechanisms are disclosed in U.S. Pat. Nos. 3,987,798; 4,045,058; 4,235,229; 4,246,897; 4,287,891; 4,307,903; and 4,315,505. The connecting lock mechanisms disclosed in the above listed patents suffer from one or more of the following disadvantages:

(1) They are not adaptable so as to be used with tubes or hoses of various sizes;

(2) They are not easily fastened;

(3) They are not quickly and easily releasable; and (4) They cannot be applied without disconnecting the endotracheal tube from the respirator.

Thus, there is a need for a connecting lock mechanism for maintaining a physical connection between an endotracheal tube and a respirator that does not have any of the above-listed disadvantages.

OBJECTS AND SUMMARY OF THE INVENTION

In view of the foregoing limitations and shortcomings of the prior art devices, as well as other disadvantages not specifically mentioned above, it should be apparent that there still exists a need in the art for an easy to use and adaptable connecting lock mechanism for an endotracheal tube/respirator tubing connector.

It is, therefore, a primary object of this invention to provide an endotracheal tube/respirator tubing connector lock that is adaptable to tubes of various sizes.

It is a further object of the present invention to provide an endotracheal tube/respirator tubing connector lock that is easy to connect and disconnect.

Still another object of the present invention is to provide an endotracheal tube/respirator tubing connector lock that can be disconnected quickly in case of emergencies.

It is yet another object of the present invention to provide an endotracheal tube/respirator tubing connector lock that can be applied without having to disconnect the endotracheal tube from the respirator.

A further object of the present invention is to provide an endotracheal tube/respirator tubing connector lock that can be fastened and removed without tools.

Briefly described, those and other objects are accomplished according to the invention by providing a connector lock mechanism comprising two clamp mechanisms and an interconnecting strap. Preferably, the lock mechanism of the present invention is formed of a one-piece resilient plastic.

One of the clamp mechanisms is a quick release clamp comprising a belt having tooth-like notches on one side of one end and a notch engaging lever at its other end. To operate the clamp, the notched end of the belt is fed through an opening adjacent the notch engaging lever and the lever is folded over on top of the notches until a shoulder on the lever engages with one of the notches to prevent the notched end of the belt from slipping back through the opening. A clip holds the lever in place while it is engaging the notches.

The quick release clamp is positioned around the rigid plastic respirator connector at a location adjacent the end that is connected to the endotracheal tube. The notched end of the belt is placed through the opening and the belt is tightened around the respirator connector and then locked in place with the lever.

The second clamp mechanism comprises a beaded chain that has a locking nut attached to one end thereof. The locking nut has a chain slot in one side and projecting from a second side are two wing lock ears that face in opposite directions. The chain is connected by a strap to the quick release clamp described above.

The beaded chain is positioned around the endotracheal tube over the region in which the semi-rigid plastic coupling extends. To lock the chain onto the endotracheal tube, the chain is wrapped around the tube and the free end of the chain is inserted into the chain slot in the nut. The nut is then twisted until the chain tightly grips the endotracheal tube, and the wing locks ears of the nut are then snapped behind the chain so that they engage with the chain so as to prevent the nut from untwisting, which would thus loosen the chain.

To release the endotracheal tube from the respirator tubing, the quick release clamp is removed by releasing the lever from the clip, lifting it out of engagement with the notches, and pulling the belt out through the opening to loosen its grip on the respirator connector. The endotracheal tube, the plastic coupling and the locking means can then be easily removed from the respirator tubing connector.

With the foregoing and other objects, advantages and features of the invention that will become hereinafter apparent, the nature of the invention may be more clearly understood by reference to the following detailed description of the invention, the appended claims and to the several views illustrated in the attached drawings.

BRIEF DESCRIPTION OF THE DRAWINGS

FIG. 1 is a perspective view of a respirator connector connected to an endotracheal tube with a plastic coupling and the locking mechanism of the present invention;

FIG. 2 is a plan view of the locking mechanism of the present invention;

FIG. 3 is a side elevational view of the locking mechanism of the present invention (partly in section) taken along line 3—3 of FIG. 2;

FIG. 4 is a side elevational view partly in section of the beaded chain and nut;

FIG. 5 is a detailed view of the lock nut used in the present invention;

FIG. 6 is a perspective view of the locking mechanism of the present invention (partly in section) in a released mode; and FIG. 7 is a perspective view of the locking mechanism of the present invention (partly in section) in a locked mode.

DETAILED DESCRIPTION OF A PREFERRED EMBODIMENT

Referring now in detail to the drawings wherein like parts are designated by like reference numerals throughout, there is illustrated in FIG. 1 a respirator connector 10 connected to an endotracheal tube 12 by means of a semi-rigid coupling 16 and locked in that position by a locking mechanism 14 according to the present invention. The semi-rigid coupling 16 has a first end comprising a tubular projection 18 that fits within the respirator connector 10, and a second tapered end 20 over which the endotracheal tube is mounted. Ends 18, 20 of coupling 16 are connected to their respective elements by a force friction fit. The function of the locking mechanism 14 is to prevent the respirator connector 10 and the endotracheal tube 12 from being inadvertently separated from the coupling 16.

Referring now to FIGS. 2-7, the design and operation of the locking mechanism 14 will now be explained.

A flexible retention strap 22 interconnects a quick release clamp mechanism 24 to a second clamp mechanism 26. The quick release clamp mechanism 24 comprises a belt 28 integrally connected at its midpoint to one end of the retention strap 22. The lower end of belt 28 is provided with a plurality of spaced notches 30 on the outer surface thereof. At the other end of the belt 28 a notch engaging mechanism is provided comprising an opening 32, a lever 34 having a sharp shoulder 36, and a flexible lever clip 38. The bever 34 is shown in cross-section in FIGS. 3, 6 and 7.

To operate the quick release clamp 24, the belt is positioned around location A (see FIG. 1) on the respirator connector 10, and the notched end of the belt 28 is inserted through the opening 32 at the other end of the belt 28. The belt 28 is pulled tightly around the respirator connector 10, and the lever 34 is folded down onto the notched end of the belt so that the sharp shoulder 36 catches one of the notches 30, thus locking the belt in place. A small convex protuberance 40 adjacent the opening 32 causes the belt to stretch slightly as the lever 34 is folded down, thus imparting additional tension to the belt 28. To prevent the belt from being accidentally released, the lever 34 is clipped within the flexible clip 38.

The second locking clamp 26 which is secured to flexible tube 12 comprises a molded beaded chain 42 integrally connected at its midpoint to the other end of the retention strap 22. One end of the chain 42 is free and the remaining end is integrally connected to a locking nut 44. The locking nut 44 has a chain slot 46 extending along one side thereof, and projecting from an adjacent side are two wing lock ears 48 which face in opposite directions.

As shown in FIGS. 6 and 7, to operate the second clamp mechanism 26, the beaded chain 42 is wrapped around the endotracheal tube 12 at location B (see FIG. 1), i.e., over the region in which the coupling 16 extends within the tube 12. The free end of the chain 42 is pulled into the chain slot 46 in the locking nut 44, and the nut 44 is then twisted to create tension within the chain 42. When the desired tension has been obtained, the wing lock ears 48 of the locking nut 44 are snapped behind the chain 42 to prevent the locking nut 44 from untwisting.

Additional frictional resistance is provided by raised molded edges 50 situated on the chain 42 and the belt 28. The raised edges 50 help to maintain a firm grip on the endotracheal tube 12 and the respirator connector 10.

To disconnect the endotracheal tube from the respirator, the lever 34 on the quick release clamp 24 is removed from the clip 38 and lifted off of the notched end of the belt, which is then slid out through the opening 32. This effectively loosens the grip of the clamp 24 from the respirator connector 10, allowing the endotracheal tube 12 to be disconnected therefrom in a conventional manner. Because of the simplicity of clamp 24, the locking mechanism 14 can be removed very quickly in case of emergencies.

The endotracheal tube/respirator locking mechanism 14 can be molded in one piece out of resilient plastic, e.g., polyethylene, polypropylene, or polyamide, or any other suitable material. If additional tensile srength is required, particularly in the chain 42, a fibrous core of high strength material such as fiberglass or even metal could be insert molded within the plastic.

What we claim is:

1. A connecting lock mechanism for locking an endotracheal tube to a respirator connector, comprising:

belt means having opposite ends and adapted to surround one of an endotracheal tube and a respirator connector and including latch means for attaching said opposite ends together in a quickly releasable manner and thereby secure said belt means around said one of an endotracheal tube and a respirator connector in a tightenable manner;

adjustable collar means for surrounding the other of the endotracheal tube and the respirator connector in a tightenable manner;

interconnection means substantially lateral to and interconnecting the belt means and the collar means;

wherein said latch means comprises notches on one end of the belt means and a notch engaging and holding lever on the other end of the belt means.

2. The connecting lock mechanism according to claim 1, wherein the end of the belt means having an opening adjacent the notch engaging lever into which passes the end of the belt means having the notches, said notch engaging lever includes a shoulder engageable with each of said notches.

3. The connecting lock mechanism according to claim 2, further comprising flexible clip means on the belt means for holding the lever in an engaged position.

4. The connecting lock mechanism according to claim 1, wherein said collar means comprises a beaded chain connected at an intermediate position thereof to the interconnection means and a locking nut attached to one end of the beaded chain, said locking nut having a chain slot therein adapted to receive and engage said beaded chain, said locking nut capable of being twisted to a locking position in which tension is applied to said chain around said one of an endotracheal tube and a respirator connector, and to an unlocked position, said locking nut including means for holding said locking nut in said locked position.

5. The connecting lock mechanism according to claim 4, further comprising raised molded edges on said belt means, the raised molded edges adapted to make frictional contact with the endotracheal tube or the respirator connector, and the beaded chain adapted to grip the endotracheal tube.

6. The device according to claim 4, wherein said means for holding said locking nut in its locked position comprises two wing lock ears projecting in opposite directions therefrom which are snapped behind the chain to prevent the locking nut from untwisting.

7. The connecting lock mechanism according to claim 1, wherein the connecting lock mechanism is of one piece molded construction of resilient plastic.

8. The connecting lock mechanism according to claim 7, wherein the connecting lock is reinforced with glass fiber to impart strength.

9. The connecting lock mechanism according to claim 7, wherein the connecting lock is reinforced with metal to impart strength.

10. The connecting lock mechanism according to claim 8, and further comprising:
a respirator connector adapted to be pneumatically connected to a respirator;
a coupling having one end removably connected to the respirator connector and a second end adapted to fit within the endotracheal tube;
said belt means connected to one of the respirator connector and the endotracheal tube;
said adjustable collar means connected to the other of the endotracheal tube and the respirator connector;
whereby when the belt means and collar means are connected to the respirator connector and the endotracheal tube, the interconnecting means impedes an accidental uncoupling of the respirator and the endotracheal tube.

11. The device according to claim 10, wherein the interconnection means comprises a strap.

12. The device according to claim 10, wherein the belt means, the collar means and the interconnecting means are of one piece molded construction of a resilient plastic.

13. The device according to claim 12, wherein the plastic is reinforced with glass fiber to impart strength.

14. The device according to claim 12, wherein the plastic is reinforced with metal to impart strength.

15. The device according to claim 1, wherein each of said belt means and collar means are quick release elements.

16. The device according to claim 1, wherein the interconnection means comprises a strap.

17. A method of impeding the accidental uncoupling of a respirator from an endotracheal tube with a connecting lock mechanism comprising belt means having opposite ends and adapted to surround one of an endotracheal tube and a respirator connector and including latch means for attaching said opposite ends together in a quickly releasable manner and thereby secure said belt means around said one of an endotracheal tube and a respirator connector in a tightenable manner; adjustable collar means for surrounding the other of the endotracheal tube and the respirator connector in a tightenable manner; interconnection means substantially lateral to and interconnecting the belt means and the collar means and wherein said latch means comprises notches on one end of the belt means and a notch engaging and holding lever on the other end of the belt means, comprising the steps of:
coupling the endotracheal tube to a respirator connector;
applying the belt means to surround one of the respirator connector and the endotracheal tube and attaching the ends of said belt means with said latch means;
applying the collar means to surround the other of the respirator connector and the endotracheal tube; and
adjusting the collar means so that it fits tightly around the other of the respirator connector and the endotracheal tube.

18. The method according to claim 17, further comprising the step of locking a lever of the belt means within a clip.

19. The method according to claim 18, further comprising the step of twisting the collar means to tighten it around the other of the respirator connector and the endotracheal tube.

* * * * *